US012544106B2

(12) United States Patent
Zhang et al.

(10) Patent No.: US 12,544,106 B2
(45) Date of Patent: Feb. 10, 2026

(54) PUNCTURE GUIDE NEEDLE

(71) Applicant: ZHEJIANG KINDLY MEDICAL DEVICES CO., LTD., Zhejiang (CN)

(72) Inventors: Yong Zhang, Zhejiang (CN); Qian Zhang, Zhejiang (CN); Hong Chen, Zhejiang (CN); Xu Chen, Zhejiang (CN); Zhuoyuan Lou, Zhejiang (CN); Zhongshichao Chi, Zhejiang (CN); Xinlin Xiang, Zhejiang (CN); Yizhang Pan, Zhejiang (CN)

(73) Assignee: ZHEJIANG KINDLY MEDICAL DEVICES CO., LTD., Wenzhou (CN)

( * ) Notice: Subject to any disclaimer, the term of this patent is extended or adjusted under 35 U.S.C. 154(b) by 159 days.

(21) Appl. No.: 18/226,751

(22) Filed: Jul. 26, 2023

(65) Prior Publication Data

US 2023/0380864 A1 Nov. 30, 2023

(30) Foreign Application Priority Data

May 26, 2022 (CN) ......................... 202210587869.5

(51) Int. Cl.
*A61B 17/34* (2006.01)

(52) U.S. Cl.
CPC ................................ *A61B 17/3468* (2013.01)

(58) Field of Classification Search
CPC .......... A61B 5/150412; A61B 5/15113; A61B 5/15115; A61B 5/15117; A61B 5/1513; A61B 5/15101; A61B 5/15111; A61B 5/15144; A61B 5/15142; A61B 5/15188; A61B 5/15186; A61B 5/1519; A61B 5/15192; A61B 5/15194; A61B 5/15196;
(Continued)

(56) References Cited

U.S. PATENT DOCUMENTS

| | | | | | |
|---|---|---|---|---|---|
| 6,443,929 | B1 * | 9/2002 | Kuracina | A61B 5/154 | 604/192 |
| 2003/0158520 | A1 * | 8/2003 | Safabash | A61M 5/158 | 604/116 |
| 2008/0051730 | A1 * | 2/2008 | Bikovsky | A61M 5/1413 | 604/240 |

FOREIGN PATENT DOCUMENTS

| | | | |
|---|---|---|---|
| CN | 110251395 | A | 9/2019 |
| CN | 215608327 | U | 1/2022 |
| CN | 215916016 | U | 3/2022 |

(Continued)

OTHER PUBLICATIONS

International Search Report of PCT.
Written Opinion of PCT.

*Primary Examiner* — Thomas McEvoy

(57) ABSTRACT

The present disclosure provides a puncture guiding needle. The puncture guiding needle includes a needle guard, a needle seat assembly, a first spring and a support, wherein the needle seat assembly and the first spring are disposed inside the needle guard; one end of the needle guard is detachably connected to the support; the needle guard is provided with a first clamping structure; a pressing portion is connected to the first clamping structure; the pressing portion is located outside the needle guard; the needle seat assembly is provided with a second clamping structure which is in clamping connection with the first clamping structure; a needle tube is disposed at one end of the needle seat assembly close to the support; the first spring is sandwiched between the needle guard and the end of the needle seat assembly away from the support.

9 Claims, 7 Drawing Sheets

(58) Field of Classification Search
CPC ............ A61B 5/15198; A61B 5/15107; A61B 5/150419; A61B 17/3468
See application file for complete search history.

(56) References Cited

FOREIGN PATENT DOCUMENTS

| | | | |
|---|---|---|---|
| CN | 216124975 | U | 3/2022 |
| JP | 2014200473 | A | 10/2014 |
| JP | 2019154953 | A | 9/2019 |

* cited by examiner

PUNCTURE GUIDE NEEDLE

CROSS-REFERENCE TO RELATED APPLICATION

This application claims priority 2022105878695, filed May 26, 2022, the content of which is incorporated herein in the entirety by reference.

TECHNICAL FIELD

The present disclosure relates to the technical field of medical devices, and more particularly, to a puncture guiding needle.

BACKGROUND

With the development of medicine, human beings have mastered many medical methods, one of which is "body-on-a-chip" (hereinafter referred to as a chip). The chip has recorded personal information therein, and the content inside can be displayed with a specific machine. The chip can provide medical history, allergy history and other information, and can be handled in time according to actual situations in emergent cases to avoid diagnostic errors; can also realize the monitoring of human health status and timely report the situations to hospitals and other ambulance units; and can monitor the conditions of transplanted organs in the body, and the like.

However, at present, doctors still use scalpels to slice skin tissues and implant chips into the human body, such that the implantation process is cumbersome and takes up the doctor's time.

SUMMARY OF THE DISCLOSURE

The present disclosure solves the problem of how to easily and quickly implant a chip into the human body to save the doctor's time.

To solve the above problem, the present disclosure provides a puncture guiding needle. The puncture guiding needle includes a needle guard, a needle seat assembly, a first spring and a support, wherein the needle seat assembly and the first spring are disposed inside the needle guard; one end of the needle guard is detachably connected to the support; the needle guard is provided with a first clamping structure; a pressing portion is connected to the first clamping structure; the pressing portion is located outside the needle guard; the needle seat assembly is provided with a second clamping structure which is in clamping connection with the first clamping structure; a needle tube is disposed at one end of the needle seat assembly close to the support; the first spring is sandwiched between the needle guard and the end of the needle seat assembly away from the support; the first spring is suitable for being in a compressed state; the support is provided with a puncture hole corresponding to the needle tube, and the puncture hole is configured to allow the needle tube to extend out; and upon the pressing portion being pressed, the pressing portion drives the first clamping structure to be away from the second clamping structure.

The present disclosure has the following technical effects: when the puncture guiding needle is used to implant the chip into the human body, a chip holder can be installed at one end of the needle seat assembly close to the support first, the chip is installed in the needle tube, and then the support is placed on the human skin surface; the pressing portion is pressed, such that the first clamping structure and the second clamping structure are disengaged from the clamping connection to excite the first spring; the first spring drives the needle seat assembly to move in a direction close to the support, so that the needle tube extends from the puncture hole and punctures into the human body to insert the chip into the human body; and finally, the needle guard is detached from the support, the chip holder is installed on the support, the needle tube is withdrawn from the human body, and the chip is left in the human body. Therefore, the puncture guiding needle can automatically complete an operation of implanting the chip into the human body, which is convenient and quick to use, and can be operated without a doctor.

Further, the needle seat assembly comprises a slider, a needle seat and a second spring; one end of the slider is in contact with the first spring; the needle seat is in clamping connection with one end of the slider away from the support; the needle tube is installed on the needle seat, and disposed in the slider in a penetrating manner; the second spring is disposed in the needle seat, is sandwiched between the needle seat and the slider and is suitable for being in a compressed state; a first triggering structure is disposed at one end of the slider close to the support, and a second triggering structure is disposed at one end of the support close to the slider; and upon the needle tube extending out of the needle guard, the first triggering structure is in contact with the second triggering structure, and drives the slider and the needle seat to disengage from the clamping connection, and the second spring drives the needle tube to retract into the needle guard.

Further, the slider is provided with a first limiting protrusion, the needle seat is provided with a second limiting protrusion, and the first limiting protrusion is pressed against one end of the second limiting protrusion away from the support; the first triggering structure comprises a triggering bump, wherein the triggering bump protrudes toward a direction close to the support; the second triggering structure comprises a triggering slope, wherein the triggering slope extends obliquely toward a direction away from the slider; and upon the needle tube protruding out of the needle guard, the triggering bump moves along the trigger slope, and the trigger bump drives the slider to rotate.

Further, the triggering bump is provided with an inclined surface at one end toward the triggering slope, and the inclined surface and the triggering slope are used to fit each other.

Further, a first annular protrusion and a second annular protrusion are disposed at one end of the slider away from the support; the second annular protrusion is located inside the first annular protrusion, and the first annular protrusion and the second annular protrusion are spaced from each other; the needle seat is inserted between the first annular protrusion and the second annular protrusion; and the needle tube is inserted into the second annular protrusion and extends out of the slider.

Further, the first clamping structure comprises a connecting portion and a clamping portion; one end of the connecting portion is connected to an outer wall of the needle guard, and the other end of the connecting portion is connected to the clamping portion and the pressing portion; a side wall of the needle guard is provided with a first hollow; and the clamping portion is configured to extend into the first hollow and in clamping connection with the second clamping structure.

Further, the clamping portion is provided with a clamping groove, the second clamping structure comprises a clamping block, and the clamping block is in clamping connection with the clamping groove; and the first hollow extends toward a direction close to the support, and the first hollow is configured to allow the clamping block to move.

Further, the puncture guiding needle further comprises a limiting ring which sleeves the needle sleeve; the limiting ring is configured to rotate around the needle sleeve; the limiting ring is provided with a limiting block; and the limiting block is located between the pressing portion and the outer wall of the needle sleeve and is pressed against the pressing portion.

Further, a magnet is disposed at one end of the support close to the needle seat assembly, and configured to adsorb a chip holder.

Further, a lug boss structure is disposed at one end of the needle guard close to the support; the support is provided with a narrow groove rail and a wide groove rail which are communicated with each other; the lug boss structure is configured to be inserted into the wide groove rail and moves into the narrow groove rail along the wide groove rail, such that the support and the needle guard are fixed.

Figure 1:
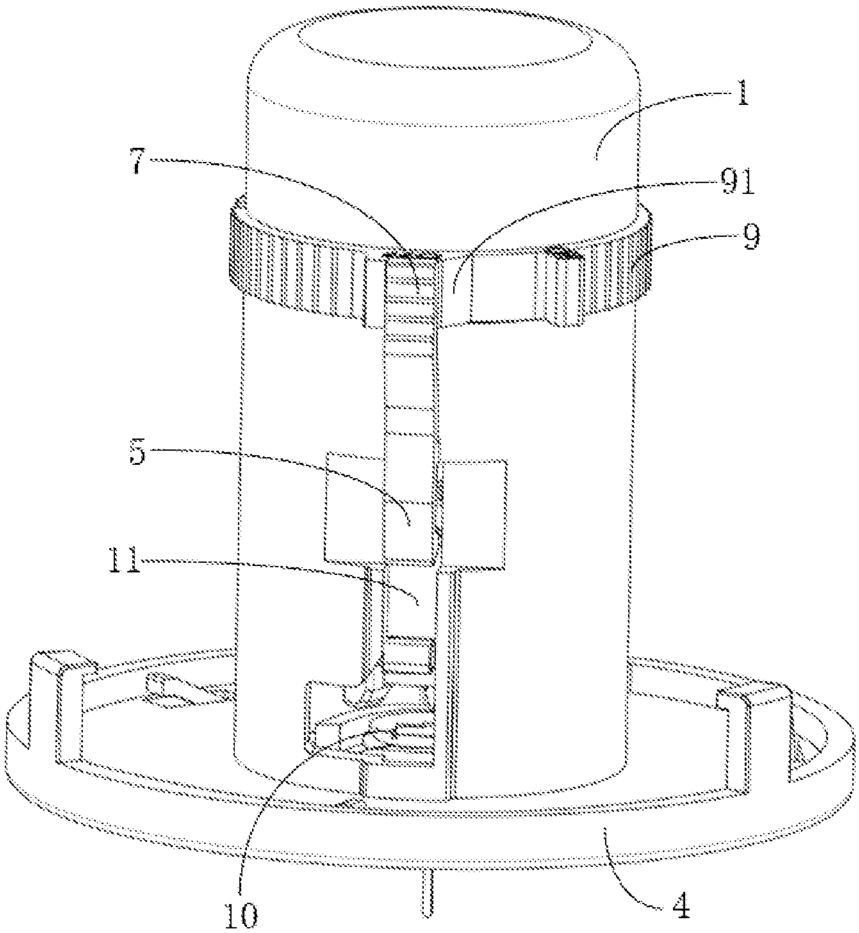
FIG. 1 is a perspective view of a puncture guiding needle from a first perspective according to an embodiment of the present disclosure.

Reference symbols represent the following components: 1—needle guard; 11—first hollow; 2—needle seat assembly; 21—slider; 211—first limiting protrusion; 212—triggering bump; 213—first annular protrusion; 214—second annular protrusion; 22—needle seat; 221—second limiting protrusion; 23—second spring; 3—first spring; 4—support; 41—puncture hole; 42—triggering slope; 43—narrow groove rail; 44—wide groove rail; 45—magnet; 5—first clamping structure; 51—connecting portion; 52—clamping portion; 6—second clamping structure; 61—clamping block; 7—pressing portion; 8—needle tube; 9—limiting ring; 91—limiting block; and 10—chip assembly.

DETAILED DESCRIPTION OF THE DISCLOSURE

In order to make the above objectives, features and advantages of the present disclosure clearer, the specific embodiments of the present disclosure are described in detail in conjunction with the accompanying drawings.

It should be noted that the terms "first", "second" and the like in the description and claims, as well as the above-mentioned drawings, of the present disclosure are used to distinguish similar objects, but not necessarily used to describe a specific order or precedence order. It should be understood that data used in this way may be interchanged where appropriate so that the embodiments of the present disclosure described herein can be implemented in a sequence other than those illustrated or described herein.

Referring to FIG. 1 to FIG. 4, an embodiment of the present disclosure provides a puncture guiding needle. The puncture guiding needle includes a needle guard 1, a needle seat assembly 2, a first spring 3 and a support 4, wherein the needle seat assembly 2 and the first spring 3 are disposed inside the needle guard 1; one end of the needle guard 1 is detachably connected to the support 4; the needle guard 1 is provided with a first clamping structure 5; a pressing portion 7 is connected to the first clamping structure 5; the pressing portion 7 is located outside the needle guard 1; the needle seat assembly 2 is provided with a second clamping structure 6 which is in clamping connection with the first clamping structure 5; a needle tube 8 is disposed at one end of the needle seat assembly 2 close to the support 4; the first spring 3 is sandwiched between the needle guard 1 and the end of the needle seat assembly 2 away from the support 4; the first spring 3 is suitable for being in a compressed state; the support 4 is provided with a puncture hole 41 corresponding to the needle tube 8, and the puncture hole 41 is configured to allow the needle tube 8 to extend out; and upon the pressing portion 7 being pressed, the pressing portion 7 drives the first clamping structure 5 to be away from the second clamping structure 6.

Specifically, the needle guard 1 may be in a cylindrical shape, wherein one end of the needle guard 1 is closed, the other end thereof is open, and the open end of the needle guard 1 is detachably connected to the support 4. In this embodiment, the needle guard 1 and the support 4 can be detachably connected by a bolt or buckle. In other embodiments, the needle guard 1 and the support 4 can be detachably connected by other ways. In this embodiment, the first clamping structure 5 may be disposed in the middle area of the needle guard 1. Two first clamping structures 5 may be symmetrically arranged with respect to an axis of the needle guard 1. In other embodiments, other numbers of first clamping structure 5 may be arranged, wherein the positions of the first clamping structures 5 on the needle guard 1 may be adaptively changed according to actual situations.

The needle seat assembly 2 may be movably disposed inside the needle guard 1, and may move in a height direction of the needle guard 1. In this embodiment, the needle seat assembly 2 may be provided with two second clamping structures 6 which are symmetrically arranged. In other embodiments, other numbers of the second clamping structures 6 may be arranged. The number of the second clamping structures 6 is equal to the number of the first clamping structures 5. When the first clamping structures 5 are in clamping connection with the second clamping structures 6, a puncture space is formed between the needle seat assembly 2 and the support 4. The puncture space can be configured to allow the needle seat assembly 2 to move and accommodate the needle tube 8, which can avoid an accidental injury of the needle tube 8 to a person when the puncture guiding needle is not in use.

The first spring 3 may be disposed in the needle guard 1, wherein one end of the first spring 3 may be in contact with an inner wall of the needle guard 1 directly opposite the support 4, and the other end of the first spring 3 may be in contact with one end of the needle seat assembly 2 away from the support 4. That is, the needle seat assembly 2 and the needle guard 1 clamp the first spring 3, such that the first spring 3 is in a compressed state. The first spring 3 is configured to drive the needle seat assembly 2 to move toward a direction close to the support 4, so that the needle tube 8 extends out of the needle guard 1.

When the chip needs to be implanted into the human body using the puncture guiding needle, the chip can be installed in the needle tube 8, the support 4 is placed on a skin tissue to be implanted with the chip, and the pressing portion 7 is pressed to make the first clamping structure 5 and the second clamping structure 6 disengaged from the clamping connection to excite the first spring 3; and the first spring 3 drives the needle seat assembly 2 to move in a direction close to the support 4, so that the needle tube 8 punctures into the human body and inserts the chip into the human body. Therefore, the above-mentioned puncture guiding needle can automatically implant the chip into the human body, which can save the doctor's time.

Referring to FIG. 3 to FIG. 8, in some embodiments, the needle seat assembly 2 includes a slider 21, a needle seat 22 and a second spring 23; one end of the slider 21 is in contact with the first spring 3; the needle seat 22 is in clamping connection with one end of the slider 21 away from the support 4; the needle tube 8 is installed on the needle seat 22, and disposed in the slider 21 in a penetrating manner; the second spring 23 is disposed in the needle seat 22, is sandwiched between the needle seat 22 and the slider 21 and is suitable for being in a compressed state; a first triggering structure is disposed at one end of the slider 21 close to the support 4, and a second triggering structure is disposed at one end of the support 4 close to the slider 21; and upon the needle tube 8 extending out of the needle guard 1, the first triggering structure is in contact with the second triggering structure, and drives the slider 21 and the needle seat 22 to disengage from the clamping connection, and the second spring 23 drives the needle tube 8 to retract into the needle guard 1.

Specifically, the slider 21 may be in a cylindrical shape. One end of the slider 21 away from the support 4 may be in contact with the first spring 3, and a side wall of the slider 21 may be provided with a second clamping structure 6. A diameter of the slider 21 is slightly smaller than an inner diameter of the needle guard 1, and the slider 21 may move along the height direction of the needle guard 1. The needle seat 22 may also be in a cylindrical shape. A diameter of the needle seat 22 is smaller than a diameter of the first spring 3, and the needle seat 22 may be inserted in the first spring 3. The needle seat 22 may be provided with a cavity inside, and the second spring 23 may be installed in the cavity. The needle tube 8 may include a needle tube holder and a thin needle tube, wherein one end of the needle tube holder is fixed to the top surface inside the needle seat 22, and the needle tube holder is inserted in the second spring 23; the other end of the needle tube holder may be disposed in the slider 21 in a penetrating manner; and the thin needle tube is connected to the other end of the needle tube holder, and is located between the slider 21 and the support 4. The second spring 23 is disposed between the needle seat 22 and the slider 21. The needle seat 22 may be in clamping connection with the slider 21, such that the second spring 23 is in a compressed state. The second spring 23 is configured to drive the needle seat 22 to move in a direction away from the support 4.

When the first spring 3 drives the slider 21 to move to a preset position, the first triggering structure on the slider 21 may be in contact with the second triggering structure on the support 4, wherein the preset position refers to a position of the slider 21 at which the needle tube 8 is punctured into the human body and the chip is just inserted into the appropriate place in the human body. The process that the first triggering structure is in contact with the second triggering structure can drive the slider 21 and the needle seat 22 to disengage from the clamping connection to excite the second spring 23; and the second spring 23 may drive the needle seat 22 to move away from the support 4, the thin needle tube is automatically pulled out of the human body, and the thin needle tube may be retracted into the needle guard 1. Therefore, after the first spring 3 is excited to puncture the thin needle tube into the human body, the second spring 23 can be automatically excited, so that the second spring 23 drives the thin needle tube to be withdrawn out of the human body, which can automatically complete the action of pulling out the thin needle tube, thereby further simplifying the process of implanting the chip into the human body.

Referring to FIG. 3 to FIG. 8, in some embodiments, the slider 21 is provided with a first limiting protrusion 211, the needle seat 22 is provided with a second limiting protrusion 221, and the first limiting protrusion 211 is pressed against one end of the second limiting protrusion 221 away from the support 4; the first triggering structure includes a triggering bump 212, wherein the triggering bump 212 protrudes toward a direction close to the support 4; the second triggering structure includes a triggering slope 42, wherein the triggering slope 42 extends obliquely toward a direction away from the slider 21; and upon the needle tube 8 protruding out of the needle guard 1, the triggering bump 212 moves along the triggering slope 42, and the triggering bump 212 drives the slider 21 to rotate.

Specifically, in this embodiment, the first limiting protrusion 211 includes a vertical protrusion and a transverse protrusion which are connected to each other, wherein the vertical protrusion is perpendicular to one end of the slider 21 away from the support 4, and the transverse protrusion is perpendicular to a side wall of the transverse protrusion. The vertical protrusion, the transverse protrusion and the end surface of the slider 21 may define a U-shaped structure with an opening toward the needle tube holder. The second limiting protrusion 221 may be disposed on a side wall of the needle tube holder, and the second limiting protrusion 221 may be inserted into the U-shaped structure. That is, at this time, the slider 21 is in clamping connection with the needle seat 22, the second limiting protrusion 221 is in contact with the transverse protrusion, and the first limiting protrusion 211 can function to limit the movement of the needle seat 22 away from the support 4.

One end surface of the slider 21 close to the support 4 may be provided with a triggering bump 212, the triggering bump 212 being a thin rod-like structure. The triggering slope 42 is formed by a depression of the end surface of the support 4 in a direction away from the slider 21. The width of the triggering slope 42 is greater than the width of the triggering bump 212. In addition, when overlooking the support 4, the shape of the triggering slope 42 is a circular arc, and the axis of the circular arc, the axis of the slider 21 and the axis of the needle seat 22 are coaxial. The depth of the depression of the triggering slope 42 gradually deepens from one end to the other end.

When the slider 21 moves toward the support 4 to the preset position, the triggering bump 212 is inserted into a space where the triggering slope 42 is located. The triggering bump 212 is in contact with the triggering slope 42, and the triggering bump 212 can move along an inclination direction of the triggering slope 42. The triggering bump 212 drives the slider 21 to rotate in the movement process, and the second limiting protrusion 221 of the slider 21 in the rotation process can be detached from the above U-shaped structure. That is, the second limiting protrusion and the first limiting protrusion 211 have no overlap in the height direction of the needle guard 1. At this time, the slider 21 and the needle seat 22 are disengaged from the clamping connection, and the second spring 23 is activated to drive the needle seat 22 to move away from the support 4. Therefore, the above-mentioned structure is simple, and the second spring 23 can be smoothly excited by the above-mentioned structure.

Figure 5:
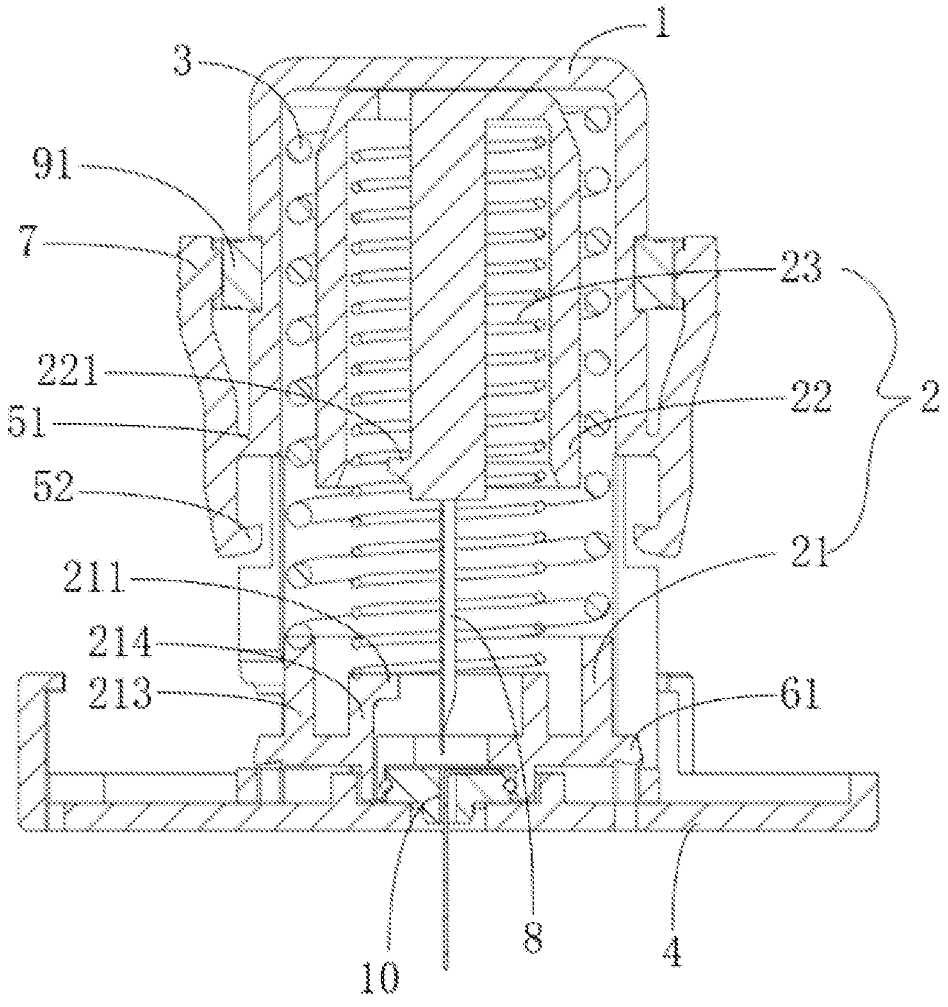
FIG. 5 is a schematic structural diagram of a needle tube retracting into a needle guard according to an embodiment of the present disclosure.
Figure 6:
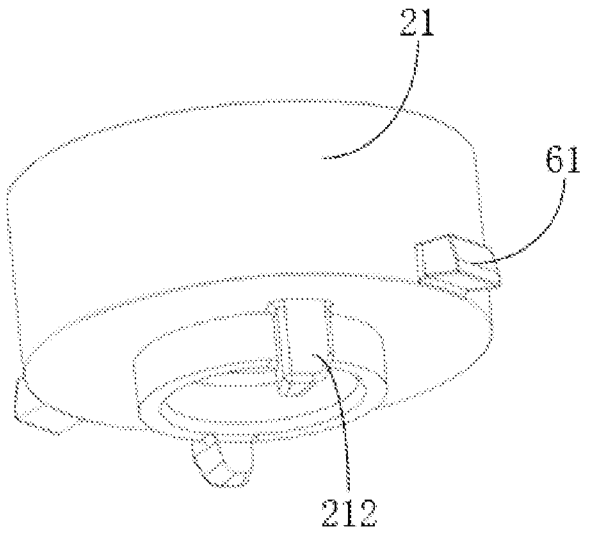
FIG. 6 is a schematic perspective view of a slider according to an embodiment of the present disclosure.
Figure 7:
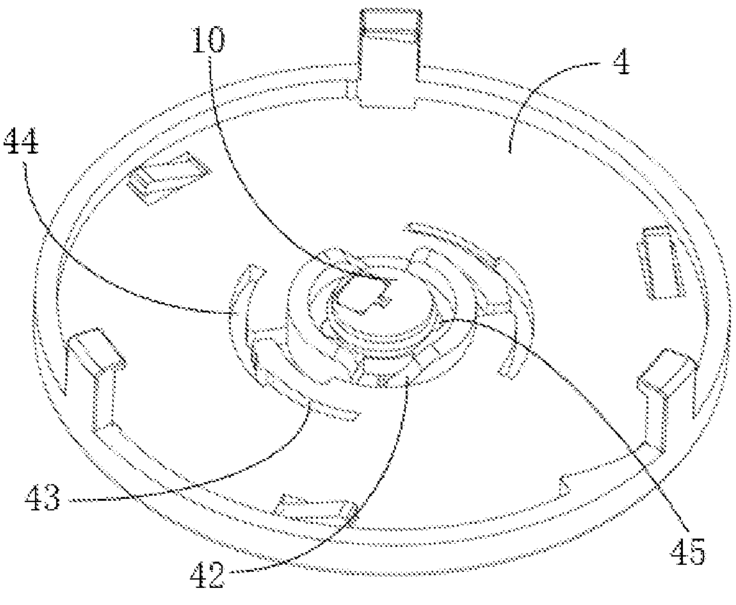
FIG. 7 is a schematic perspective view of a support according to an embodiment of the present disclosure.

Referring to FIG. 5 to FIG. 7, in some embodiments, the triggering bump 212 is provided with an inclined surface at one end toward the triggering slope 42, and the inclined surface and the triggering slope 42 are used to fit each other.

Specifically, the inclined surface is disposed at one end of the triggering bump 212 directly opposite the triggering slope 42. When the triggering bump 212 is in contact with the triggering slope 42, the inclined surface can fit the inclined surface of the triggering slope 42, such that the triggering bump 212 moves more smoothly along the triggering slope 42, which can reduce the probability of excitation failure of the second spring 23, thereby reducing a failure rate of the puncture guiding needle.

Figure 3:
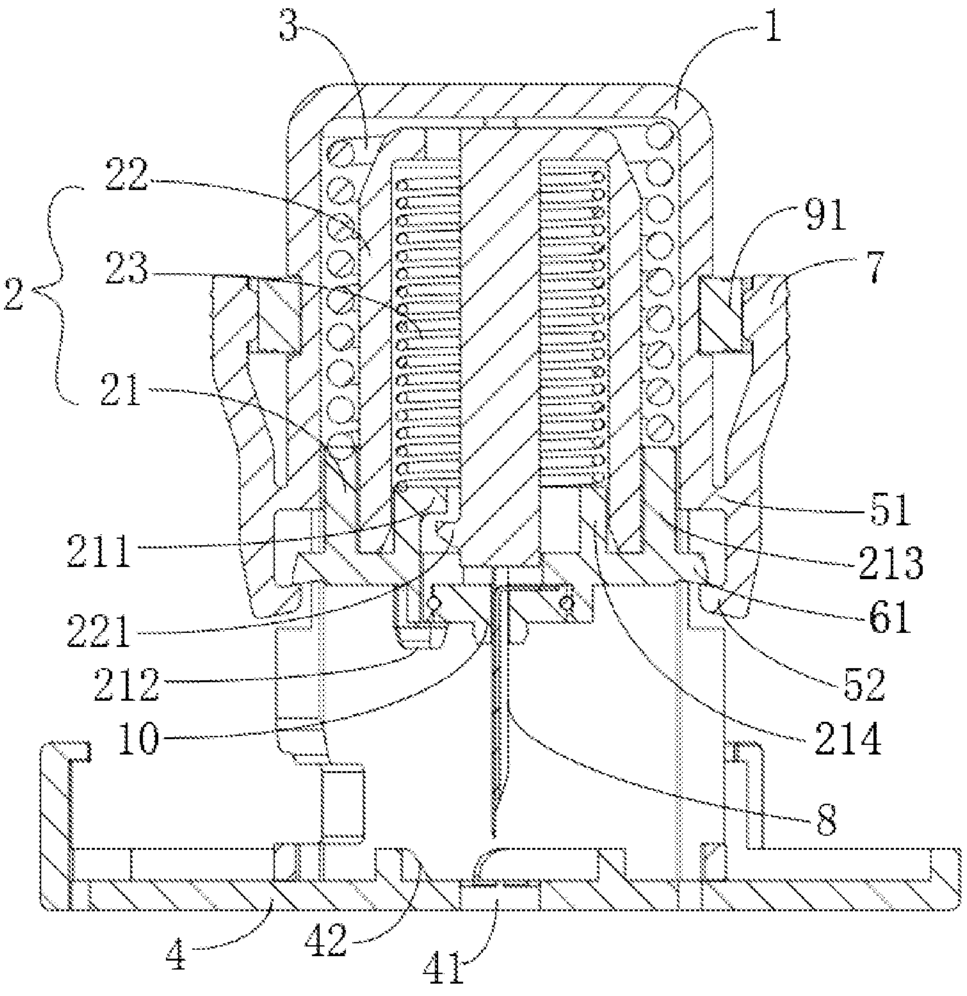
FIG. 3 is a schematic diagram of an internal structure of a puncture guiding needle according to an embodiment of the present disclosure.
Figure 4:
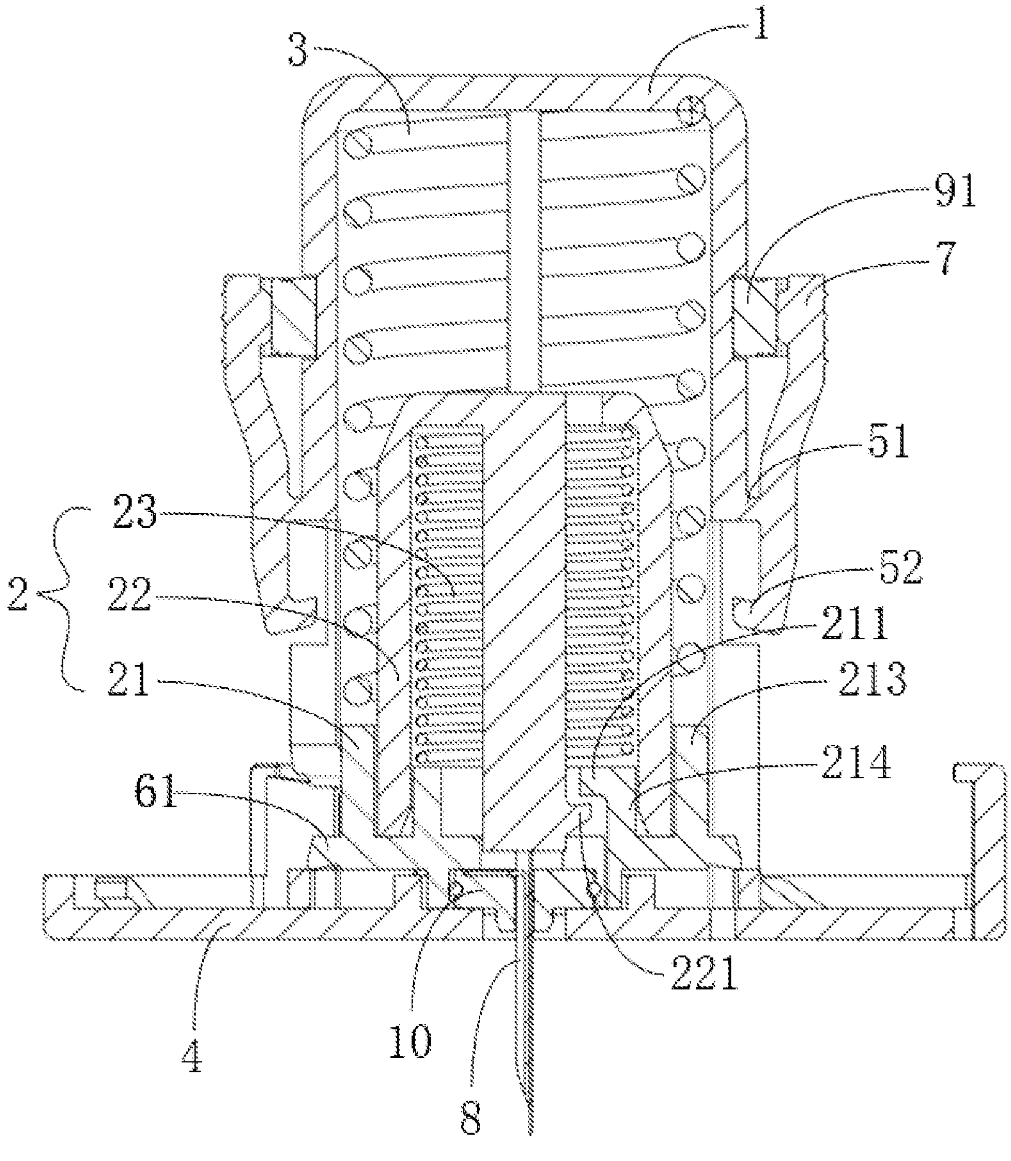
FIG. 4 is a schematic structural diagram of a needle tube extending out of a needle guard according to an embodiment of the present disclosure.

Referring to FIG. 3 to FIG. 5, in some embodiments, a first annular protrusion 213 and a second annular protrusion 214 are disposed at one end of the slider 21 away from the support 4; the second annular protrusion 214 is located inside the first annular protrusion 213, and the first annular protrusion 213 and the second annular protrusion 214 are spaced from each other; the needle seat 22 is inserted between the first annular protrusion 213 and the second annular protrusion 214; and the needle tube 8 is inserted into the second annular protrusion 214 and extends out of the slider 21.

Specifically, the end surface of the slider 21 away from the support 4 may be provided with two annular protrusions, i.e., the first annular protrusion 213 and the second annular protrusion 214. The first annular protrusion 213 and the second annular protrusion 214 are coaxial, and are spaced from each other, and the second annular protrusion 214 is located within the first annular protrusion 213. A diameter of the first annular protrusion 213 is equal to that of the first spring 3, and one end of the first annular protrusion 213 is in contact with the first spring 3. A diameter of the second annular protrusion 214 is equal to that of the second spring 23, and the second annular protrusion 214 is in contact with the second spring 23. The needle seat 22 may be inserted between the first annular protrusion 213 and the second annular protrusion 214. In addition, the slider 21 is provided with a hole in an area within the second annular protrusion, and the needle tube 8 may be disposed in the hole in a penetrating manner and extend out of the slider 21. The first limiting protrusion may be disposed on an inner wall of the second annular protrusion 214, and may be perpendicular to the second annular protrusion 214.

When the needle seat 22 needs to be in clamping connection with the slider 21, the needle seat 22 may be precisely located on the slider 21 just by inserting the needle seat 22 between the first annular protrusion 213 and the second annular protrusion 214 first and then allowing the needle tube 8 to pass through the hole in the slider 21. The second limiting protrusion 221 is then in contact with the first limiting protrusion 211 by rotating the needle seat 22, such that the clamping connection between the needle seat 22 and the slider 21 can be completed. Therefore, the needle seat 22 may be installed on the slider 21 conveniently and quickly by means of the above structure, such that the puncture guiding needle is more comfortable to use.

Figure 2:
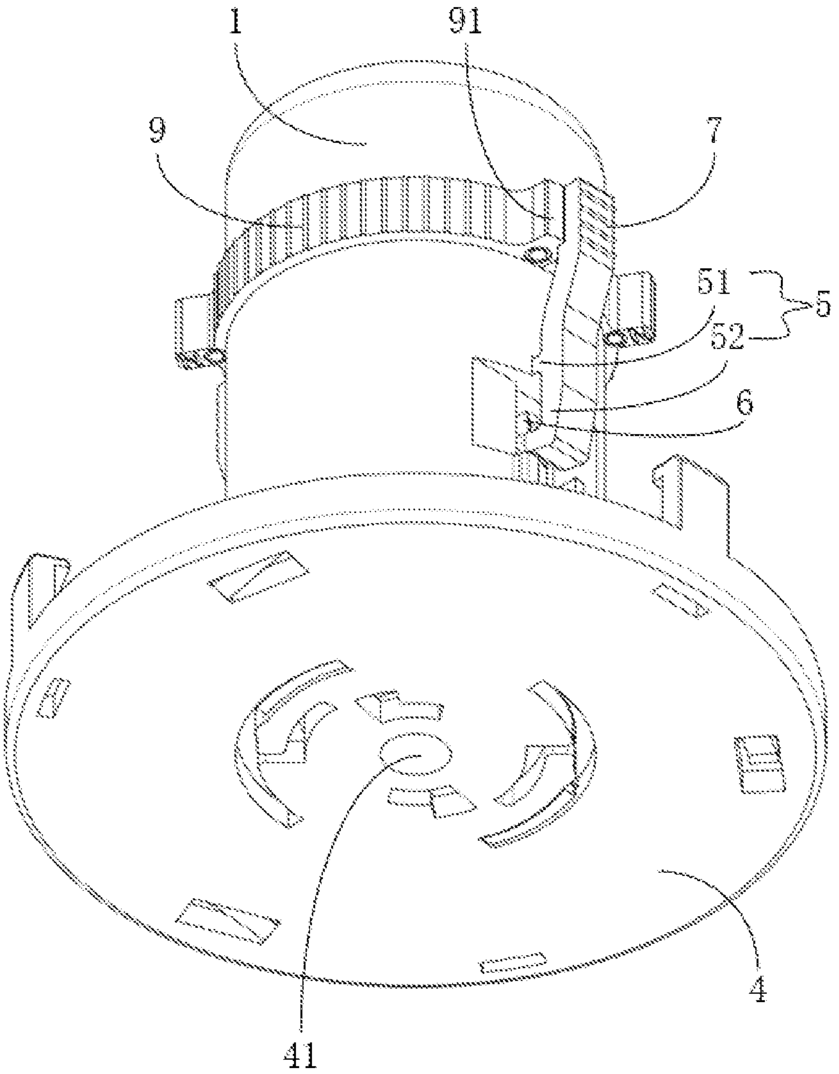
FIG. 2 is a perspective view of a puncture guiding needle from a second perspective according to an embodiment of the present disclosure.

Referring to FIG. 1 and FIG. 2, in some embodiments, the first clamping structure 5 includes a connecting portion 51 and a clamping portion 52; one end of the connecting portion 51 is connected to an outer wall of the needle guard 1, and the other end of the connecting portion 51 is connected to the clamping portion 52 and the pressing portion 7; the side wall of the needle guard 1 is provided with a first hollow 11; and the clamping portion 52 is configured to extend into the first hollow 11 and in clamping connection with the second clamping structure 6.

Specifically, the connecting portion 51 may be perpendicular to the outer wall of the needle guard 1. The connecting portion 51 may be connected to the clamping portion 52. The clamping portion 52 may be obliquely inserted into the first hollow 11 and may also be in clamping connection with the second clamping structure 6. The pressing portion 7 may be connected to the clamping portion 52, and a gap is formed between the pressing portion 7 and the outer wall of the needle guard 1. The length of the pressing portion 7 is greater than the length of the clamping portion 52. The pressing portion 7 and the clamping portion 52 may form a structure like a long rod. The connecting portion 51 may be used as a fulcrum of the long rod formed by the pressing portion 7 and the clamping portion 52. Upon the pressing of the pressing portion 7 in a direction close to the needle guard 1, the clamping portion 52 can be driven to move in a direction away from the second clamping structure 6, such that the clamping portion 52 and the second clamping structure 6 are disengaged from the clamping connection, and thus the first spring 3 can be excited. Therefore, the first spring 3 can be excited by pressing portion 7 with little effort, which is convenient for an operator to use the puncture guiding needle.

Referring to FIG. 1 and FIG. 2, in some embodiments, the puncture guiding needle further includes a limiting ring 9 which sleeves the needle guard 1. The limiting ring 9 is configured to rotate around the needle guard 1. The limiting ring 9 is provided with a limiting block 91; and the limiting block 91 is located between the pressing portion 7 and the outer wall of the needle guard 1 and is pressed against the pressing portion 7.

Specifically, the outer wall of the needle guard 1 may be provided with an annular groove in which the limiting ring 9 may be installed. In addition, the limiting ring 9 may rotate around the axis of the needle guard 1. The limiting ring 9 may be provided with the limiting block 91. The limiting block 91 may be located between the pressing portion 7 and the needle guard 1 and is pressed against the pressing portion 7. The limiting block 91 can function to limit the movement of the pressing portion 7 in the direction close to the needle guard 1, which can avoid the excitation of the first spring 3 resulting from the accidental touch against the pressing portion 7, thereby avoiding causing personal injury.

When the puncture guiding needle needs to be used, the limiting ring 9 may be rotated, such that the limiting block 91 leaves the area between the pressing portion 7 and the needle guard 1, and then, the pressing portion 7 can be pressed normally to excite the first spring 3.

Referring to FIG. 1 to FIG. 3, in some embodiments, the clamping portion 52 is provided with a clamping groove; the second clamping structure 6 includes a clamping block 61, and the clamping block 61 is in clamping connection with the clamping groove; and the first hollow 11 extends toward a direction close to the support 4, and the first hollow 11 is configured to allow the clamping block 61 to move.

Specifically, the clamping portion 52 may include a vertical clamping plate and a transverse clamping plate. The vertical clamping plate may be connected to the connecting portion 51, and may be perpendicular to the connecting portion 51. The transverse clamping plate may be fixed perpendicularly to the vertical clamping plate. In addition, the transverse clamping plate may protrude toward a direction close to the needle guard 1. The transverse clamping plate, the vertical clamping plate and the connecting portion 51 may define a clamping groove. The clamping block 61 may extend into the first hollow 11 and be in clamping connection to the clamping groove. The first hollow 11 may extend in the height direction of the needle guard 1 towards a direction close to the support 4. Upon the movement of the slider 21 toward the direction close to the support 4, the clamping block 61 may move in the first hollow 11. The first hollow 11 may function to guide the slider, which can prevent the slider 21 from rotating indiscriminately inside the needle guard 1 and causing failure, such that the failure rate of the puncture guiding needle can be reduced.

When the first hollow 11 extends to a position in contact with the support 4, it may extend along the circumference of the needle guard 1 instead. A movement space can be reserved for the rotation of the slider 21 inside the needle guard 1, which can avoid the situation that the slider 21 and the needle seat 22 cannot be disengaged from the clamping connection since the clamping block 61 is blocked and thus the slider 21 fails to rotate.

Figure 8:
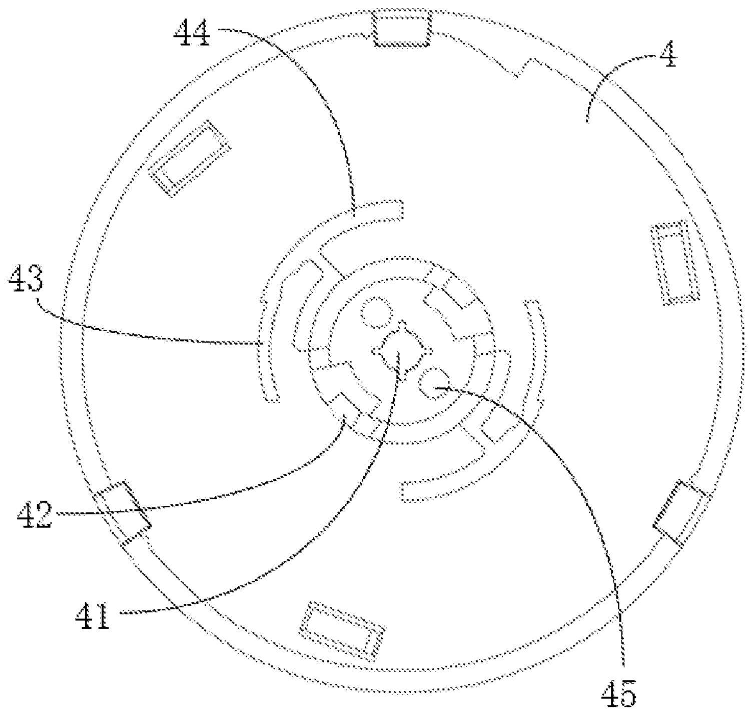
FIG. 8 is a top view of a support according to an embodiment of the present disclosure.

Referring to FIG. 7 and FIG. 8, in some embodiments, a magnet 45 is disposed at one end of the support 4 close to the needle seat assembly 2, and configured to adsorb a chip assembly 10.

Specifically, a groove may be formed in one end of the support 4 close to the needle seat assembly 2. The magnet 45 may be installed in the groove. The chip assembly 10 may include a chip holder, a chip and a magnetic metal sheet, wherein the chip and the magnetic metal sheet are installed on the chip holder. When the puncture guiding needle is used, the chip holder may be installed at one end of the slider 21 close to the support 4. The first spring 3 drives the slider 21 to move in a direction close to the support 4, such that the chip can be implanted into the human body. The magnet 45 on the support 4 may adsorb the chip holder, such that the chip holder is automatically installed on the support 4, without any manual operation. Therefore, the process of implanting the chip into the human body can be further simplified.

Referring to FIG. 2, FIG. 7 and FIG. 8, in some embodiments, a lug boss structure is disposed at one end of the needle guard 1 close to the support 4; the support 4 is provided with a narrow groove rail 43 and a wide groove rail 44 which are communicated with each other; the lug boss structure is configured to be inserted into the wide groove rail 44 and moves into the narrow groove rail 43 along the wide groove rail 44, such that the support 4 and the needle guard 1 are fixed.

Specifically, in this embodiment, two lug boss structures may be disposed at one end of the needle guard 1 close to the support 4, and two groups of narrow groove rails 43 and wide groove rails 44 are disposed on the support 4, wherein each group of narrow groove rail 43 and wide groove rail 44 corresponds to one lug boss structure. In other embodiments, other numbers of lug boss structures may be disposed at one end of the needle guard 1 close to the support 4. The number of the narrow groove rails 43 and wide groove rails 44 on the support 4 is equal to the number of the lug boss structures.

In this embodiment, each lug boss structure may include two plates which are perpendicular to each other, wherein one plate is perpendicular to the end surface of the needle guard 1, and the other plate is parallel to the end surface of the needle guard 1. The two plates and the end surface of the needle guard 1 may define a structure with grooves. In addition, the two plates may be curved plates, and the wide groove rails 44 and the narrow groove rails 43 are also curved. When the needle guard 1 is installed on the support 4, the lug boss structures are first inserted into the wide groove rails 44, and then the needle guard 1 is rotated so that the lug boss structures move along the wide groove rails 44 into the narrow groove rails 43. The grooves in each lug boss structure may be in clamping connection to the side walls of the narrow groove rails 43, so that the needle guard 1 is temporarily fixed to the support 4. When the needle guard 1 needs to be detached from the support 4, the needle guard 1 needs to be rotated reversely, and the lug boss structure moves to the wide groove rail 44 along the narrow groove rail 43, such that the needle guard 1 is detached form the support 4. In other embodiment, each lug boss structure may include three plates, two of which are parallel to each other, and the other of which is disposed perpendicularly between the two plates and connected to the two plates which are parallel to each other. The three plates may form an I-shaped structure. Therefore, due to the arrangement of the lug boss structures, the narrow groove rails 43 and the wide groove rails 44, the needle guard 1 can be detachably installed on the support 4.

Although the present disclosure discloses the following content, the protection scope of the present disclosure is not limited to this. Those skilled in the art can make modifications and changes without departing from the spirit and scope of the present disclosure, and these modifications and changes all fall within the protection scope of the present disclosure.

The invention claimed is:

1. A puncture guiding needle assembly, comprising a needle guard (1), a needle seat assembly (2), a first spring (3) and a support (4), wherein the needle seat assembly (2) and the first spring (3) are disposed inside the needle guard (1); one end of the needle guard (1) is detachably connected to the support (4); the needle guard (1) is provided with a first clamping structure (5); wherein the first clamping structure (5) comprises a finger pad (7), a connecting portion (51) and a clamping portion (52); one end of the connecting portion (51) is connected to an outer wall of the needle guard (1), the other end of the connecting portion (51) is connected to the clamping portion (52) and the finger pad (7), and the connecting portion (51) is between the clamping portion (52) and the finger pad (7); the finger pad (7) is located outside the needle guard (1); the needle seat assembly (2) is provided with a second clamping structure (6) which is in clamping connection with the first clamping structure (5); a needle tube (8) is disposed at one end of the needle seat assembly (2) closer to the support (4); the first spring (3) is sandwiched between the needle guard (1) and the other end of the needle seat assembly (2) away from the support (4); the first spring (3) is suitable for being in a compressed state; the support (4) is provided with a puncture hole (41) corresponding to the needle tube (8), and the puncture hole (41) is configured to allow the needle tube (8) to extend out; upon the finger pad (7) being pressed, the finger pad (7) drives the first clamping structure (5) to be away from the second clamping structure (6);

a side wall of the needle guard (1) is provided with a first hollow; and the clamping portion (52) is configured to extend into the first hollow and in clamping connection with the second clamping structure (6);

the clamping portion (52) is provided with a clamping groove; the second clamping structure (6) comprises a clamping block (61), and the clamping block (61) is in clamping connection with the clamping groove; and the first hollow extends toward a direction closer to the support (4), and the first hollow is configured to allow the clamping block (61) to move, the puncture guiding needle assembly further comprises a limiting ring (9) which surrounds the needle guard (1); the limiting ring (9) is configured to rotate around the needle guard (1); the limiting ring (9) is provided with a limiting block (91); and the limiting block (91) is located between the finger pad (7) and the outer wall of the needle guard (1) and is pressed against the finger pad (7).

2. The puncture guiding needle assembly according to claim 1, wherein the needle seat assembly (2) comprises a slider (21), a needle seat (22) and a second spring (23); one end of the slider (21) is in contact with the first spring (3); the needle seat (22) is in clamping connection with one end of the slider (21) away from the support (4); the needle tube (8) is installed on the needle seat (22), and disposed in the slider (21) in a penetrating manner; the second spring (23) is disposed in the needle seat (22), is sandwiched between the needle seat (22) and the slider (21) and is suitable for being in a compressed state; a first triggering structure is disposed at one end of the slider (21) closer to the support (4), and a second triggering structure is disposed at one end of the support (4) closer to the slider (21); and upon the needle tube (8) extending out of the needle guard (1), the first triggering structure is in contact with the second triggering structure, and drives the slider (21) and the needle seat (22) to disengage from the clamping connection, and the second spring (23) drives the needle tube (8) to retract into the needle guard (1); wherein the first triggering structure comprises a triggering bump (212), wherein the triggering bump (212) protrudes toward a direction closer to the support (4); the second triggering structure comprises a triggering slope (42), wherein the triggering slope (42) extends obliquely toward a direction away from the slider (21).

3. The puncture guiding needle assembly according to claim 2, wherein the slider (21) is provided with a first limiting protrusion (211), the needle seat (22) is provided with a second limiting protrusion (221), and the first limiting protrusion (211) is pressed against one end of the second limiting protrusion (221) away from the support (4); and upon the needle tube (8) extending out of the needle guard (1), the triggering bump (212) moves along the triggering slope (42), and the triggering bump (212) drives the slider (21) to rotate.

4. The puncture guiding needle assembly according to claim 3, wherein the triggering bump (212) is provided with an inclined surface at one end toward the triggering slope (42), and the inclined surface and the triggering slope (42) are used to fit each other.

5. The puncture guiding needle assembly according to claim 2, wherein a first annular protrusion (213) and a second annular protrusion (214) are disposed at one end of the slider (21) away from the support (4); the second annular protrusion (214) is located inside the first annular protrusion (213), and the first annular protrusion (213) and the second annular protrusion (214) are spaced from each other; the needle seat (22) is inserted between the first annular protrusion (213) and the second annular protrusion (214); and the needle tube (8) is inserted into the second annular protrusion (214) and extends out of the slider (21).

6. The puncture guiding needle assembly according to claim 1, wherein a lug boss structure is disposed at one end of the needle guard (1) closer to the support (4); the support (4) is provided with a narrow groove rail (43) and a wide groove rail (44) which are connected with each other; the lug boss structure is configured to be inserted into the wide groove rail (44) and moves into the narrow groove rail (43) along the wide groove rail (44), such that the support (4) and the needle guard (1) are fixed; wherein the narrow groove rail (43) and the wide groove rail (44) are arc-shaped and surround the puncture hole (41).

7. The puncture guiding needle assembly according to claim 1, wherein the support (4) comprises a groove formed in one end of the support (4) closer to the needle seat assembly 2, and a magnet (45) is installed in the groove and configured to attach a chip assembly (10).

8. The puncture guiding needle assembly according to claim 7, wherein the chip assembly (10) comprises a chip holder, a chip and a magnetic metal sheet, the chip and the magnetic metal sheet are installed on the chip holder, the chip holder is installed at one end of the slider (21) closer to the support (4).

9. The puncture guiding needle assembly according to claim 7, wherein a plurality of lug boss structures are disposed at the end of the needle guard (1) closer to the support (4), a plurality of groups of narrow groove rails (43) and wide groove rails (44) are disposed on the support (4), each lug boss structure is configured to be inserted into a corresponding wide groove rail (44), the narrow groove rails (43) and wide groove rails (44) are arranged alternately along a direction surrounding the puncture hole (41).

* * * * *